United States Patent [19]

Seele et al.

[11] Patent Number: 5,084,471

[45] Date of Patent: Jan. 28, 1992

[54] 1-HALOVINYLAZOLES AND FUNGICIDES AND GROWTH REGULATORS CONTAINING THESE

[75] Inventors: Rainer Seele; Reiner Kober, both of Fussgoenheim; Norbert Goetz, Worms; Thomas Saupe, Sandhausen; Eberhard Ammermann, Ludwigshafen; Gisela Lorenz, Neustadt; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 500,728

[22] Filed: Mar. 28, 1990

[30] Foreign Application Priority Data

Apr. 26, 1989 [DE] Fed. Rep. of Germany ....... 3913725

[51] Int. Cl.$^5$ ................. A01N 43/653; C07D 249/08
[52] U.S. Cl. .................... 514/383; 514/184; 548/101; 548/268.4
[58] Field of Search ............ 548/101, 268.4; 514/184, 383

[56] References Cited

U.S. PATENT DOCUMENTS

| 4,273,776 | 6/1981 | Hoehn | 548/341 |
| 4,360,528 | 11/1982 | Jöger et al. | 548/268.4 |
| 4,729,783 | 3/1988 | Regel et al. | 548/268.4 |
| 4,957,539 | 9/1990 | Worthington et al. | 548/267.8 |

Primary Examiner—Patricia L. Morris
Attorney, Agent, or Firm—Oblon, Spivak, McClelland, Maier & Neustadt

[57] ABSTRACT

1-Halovinylazoles of the general formula I

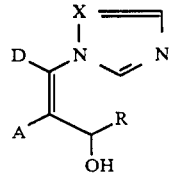

where A and R are each alkyl, cycloalkyl, cycloalkenyl, pyridyl, tetrahydropyranyl, naphthyl, biphenyl or phenyl, each of these radicals being substituted or unsubstituted, D is chlorine or bromine, and X is CH or N, acid addition salts and metal complexes thereof which are tolerated by plants, and fungicides and growth regulators containing these compounds.

7 Claims, No Drawings

1-HALOVINYLAZOLES AND FUNGICIDES AND GROWTH REGULATORS CONTAINING THESE

The present invention relates to novel azole compounds, a process for the preparation thereof, and fungicides and growth regulators containing these.

The use of vinylazoles, eg. 1-(1,2,4-triazol-1-yl)-2-(4-chlorobenzyl)-3-phenyl-1-propen-3-ol or 1-(1,2,4-triazol-1-yl)-2-(4-chlorophenyl)-3-(2,4-dichlorophenyl)-1-propen-3-ol, as fungicides has been disclosed (EP 23,286). Their action is unsatisfactory, however We have now found that 1-halo-1-vinylazoles of the formula I

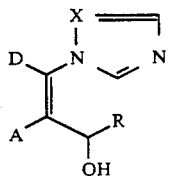

where A and R are identical or different and are $C_1-C_8$-alkyl, $C_5-C_8$-cycloalkyl, $C_5-C_8$-cycloalkenyl, tetrahydropyranyl, pyridyl, naphthyl, biphenylyl or phenyl, it being possible for these radicals to be substituted (1 to 3 times) by halogen, nitro, phenoxy, amino, alkyl, alkoxy or haloalkyl of 1 to 4 carbon atoms in each case, D is chlorine or bromine, X is CH or N, and the acid addition salts or metal complexes thereof which are tolerated by plants have a better fungicidal action than known azole compounds and have a good action as growth regulators.

The compounds of the formula I contain asymmetric carbon atoms and can therefore occur as enantiomers and diastereomers. The diastereomers of the compounds according to the invention can be separated in mixtures thereof, and isolated in pure form, in a conventional manner, for example on the basis of solubility differences or by column chromatography. Racemates of the compounds according to the invention can be resolved by known methods, for example by formation of a salt with an optically active acid, separation of the diastereomeric salts and liberation of the enantiomers using a base. The pure diastereomers or enantiomers, and the mixtures thereof produced in the synthesis, can be used as fungicides and growth regulators.

Examples of A and R are methyl, ethyl, isopropyl, n-propyl, n-butyl, sec-butyl, tert-butyl, n-pentyl, neopentyl, 1-naphthyl, 2-naphthyl, p-biphenylyl, phenyl, 2-chlorophenyl, 2-fluorophenyl, 2-bromophenyl, 3-chlorophenyl, 3-bromophenyl, 3-fluorophenyl, 4-fluorophenyl, 4chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tert.butyloxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethyl-phenyl, 4-trifluoromethylphenyl, 3-pyridyl, tetrahydropyranyl, cyclopropyl, cyclopentyl, cyclohexyl, 2-cyclohexenyl and 3-cyclohexenyl.

Examples of acid addition salts are the hydrochlorides, hydrobromides, sulfates, nitrates, phosphates, oxalates or dodecylbenzenesulfonates. The activity of the salts derives from the cation, so that the anion is generally immaterial. Salts of the active ingredients according to the invention are prepared by reacting the 1-halo-1-vinylazoles I with suitable acids.

Metal complexes of the active ingredients I or salts thereof can be formed with, for example, copper, zinc, tin, manganese, iron, cobalt or nickel by reacting the 1-halovinylazoles with appropriate metal salts.

The compounds of the formula I can be prepared by rearranging a compound of the formula II

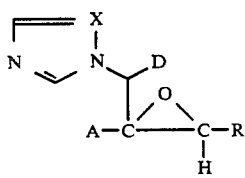

where A, R, D and X have the meaning specified above, in the presence of a base, to give the 1-halovinylazoles.

The reaction is carried out in the presence or absence of a solvent or diluent with the addition of an inorganic or organic base at from 10° to 120° C.

Preferred solvents and diluents include ketones such as acetone, methyl ethyl ketone or cyclohexanone, nitriles such as acetonitrile or propionitrile, alcohols such as methanol, ethanol, iso-propanol, n-butanol or glycol, ethers such as tetrahydrofuran, diethyl ether, dimethoxyethane, dioxane or diisopropyl ether, amides such as dimethylformamide, dimethylacetamide or N-methylpyrrolidone, sulfolane or mixtures thereof.

Examples of suitable bases are alkali metal hydroxides such as lithium, sodium or potassium hydroxide, alkali metal hydrides such as lithium, sodium and potassium hydride, alkali metal amides such as those of sodium and potassium, alkali metal carbonates such as sodium, potassium or cesium carbonate or sodium, potassium or cesium bicarbonate, also sodium or potassium tert-butoxide, and sodium or potassium methanolate.

The reaction is generally carried out at from 20° to 150° C., under atmospheric or superatmospheric pressure, continuously or batchwise.

The starting compounds II can be prepared by reacting a compound of the formula III

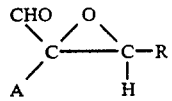

where A and B have the meanings specified above, with a compound of the formula IV

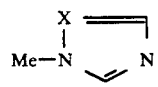

where X has the meaning specified above, and Me is hydrogen or a metal atom (eg. Na or K), in the presence of the appropriate thionyl halide.

The reaction is carried out in the presence or absence of a solvent or diluent at from −30° to 80° C. The preferred solvents and diluents include nitriles such as acetonitrile or propionitrile, ethers such as tetrahydrofuran, diethyl ether, dimethoxyethane, dioxane or diisopropyl ether and, in particular, hydrocarbons and chlorohydrocarbons such as pentane, hexane, toluene, methylene chloride, chloroform, tetrachloromethane, dichloroethane or mixtures thereof.

The novel starting compounds III are obtained by epoxidation of the corresponding olefins V

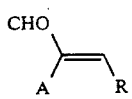

where A and B have the meanings specified above, with peroxycarboxylic acids such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid in inert solvents, preferably chlorohydrocarbons, eg. methylene chloride, chloroform, tetrachloromethane and dichloroethane, but possibly also in acetic acid, ethyl acetate, acetone or dimethylformamide, in the presence or absence of a buffer such as sodium acetate, sodium carbonate, disodium hydrogen phosphate or Triton B. The reaction is carried out at from 10° to 100° C. and can be catalyzed with, for example, iodine, sodium tungstate or light. Also suitable for the oxidation are alkaline solutions of hydrogen peroxide (about 30% strength) in methanol, ethanol, acetone or acetonitrile at from 25° to 30° C., and alkyl hydroperoxides, eg. tert-butyl hydroperoxide, with the addition of a catalyst, eg. sodium tungstate, pertungstic acid, molybdenum hexacarbonyl or vanadyl acetylacetonate. Some of the said oxidizing agents can be generated in situ.

The compounds V can be prepared by conventional processes for aldehyde synthesis (Houben-Weyl-Müller, Methoden der Organischen Chemie, Georg Thieme Verlag, Stuttgart 1983/4, Vol. E 3).

The Examples which follow illustrate the preparation of the active ingredients.

1. Preparation of the starting materials

Method 1

E/Z-2-(4-Fluorophenyl)-3-(2-chlorophenyl)propenal 4.2 g of sodium hydroxide in 30 ml of water are added to a solution of 35 g of 2-chlorobenzaldehyde in 300 ml of methanol. The reaction mixture is cooled to 10° C. and 36 g of 4-fluorophenylacetaldehyde are rapidly added, during which the solution warms to 30°-40° C. The reaction solution is stirred at 40° C. for 10 hours and then cooled, and the crystals which separate out are filtered off with suction.

Method 2 cis-2-Formyl-2-(4-fluorophenyl)-3-(2-chlorophenyl)oxirane 78.2 g of E-2-(4-fluorophenyl)-3-(2-chlorophenyl)propenal are dissolved in 300 ml of methanol, and 1 ml of sodium hydroxide solution (concentrated) is added. The reaction solution is stirred at 0° C. while 20.5 g of hydrogen peroxide (about 50% strength) are slowly added dropwise, not allowing the internal temperature to exceed 30° C. The mixture is stirred at room temperature for 6 hours after the end of the addition, and then 100 ml of water are added and the resulting emulsion is extracted with methyl tert-butyl ether. The isolated organic phase is then dried with sodium sulfate and concentrated. 52.5 g (63%) of cis-2-formyl-2-(4-fluorophenyl)-3-(2-chlorophenyl)oxirane are obtained.

Method 3

1'RS-cis-2-[1-(1,2,4-Triazol-1-yl)-1-chloromethyl]-2-(4-fluorophenyl)-3-(2-chlorophenyl)oxirane 12.8 g of thionyl chloride are added to a solution of 29.7 g of triazole in 150 ml of methylene chloride at 0° C. under a nitrogen atmosphere. The mixture is stirred at room temperature for 30 minutes after the end of the addition, and subsequently 20 g of cis-2-formyl2-(4-fluorophenyl)-3-(2-chlorophenyl)oxirane are added. The reaction mixture is stirred at room temperature for 12-15 hours and then 100 ml of water are added, and the organic phase is separated off. The remaining aqueous phase is extracted twice with methylene chloride, and the collected organic phases are washed twice with saturated sodium bicarbonate solution The isolated organic phase is then dried over sodium sulfate and concentrated, resulting in 23.7 g (85%) of cis-2-[1-(1,2,4-triazol-1-yl)-1-chloromethyl]-2-(4-fluorophenyl)-3-(2-chlorophenyl)oxirane as a 2:1 mixture of diastereomers. 5.8 g of the major diastereomer A, of melting point 152-156° C., are obtained from methyl tert-butyl ether.

II. Preparation of the final products

EXAMPLE 1

5 g of 1'RS-cis-2-[1-(1,2,4-triazol-1-yl)-1chloromethyl]-2-(4-fluorophenyl)-3-(2-chlorophenyl)-oxirane are dissolved in 100 ml of methanol, 1.7 g of sodium methylate are added, and the mixture is refluxed for one hour. The solution is then cooled to room temperature, 100 ml of water are added, and the mixture is extracted several times with methyl tert-butyl ether. The isolated organic phase is washed twice with water and then dried over sodium sulfate and concentrated, resulting in 4.4 g (87%) of 1-chloro-1-(1,2,4-triazol-1-yl)-2-(4-fluorophenyl)-3-(2-chlorophenyl)propen-3-ol (compound No. 1), melting point 153°-156° C.

The compounds listed in the table can be prepared as in Example 1.

TABLE

| Ex | A | R | D | X | m.p./IR (cm$^{-1}$) |
|---|---|---|---|---|---|
| 1 | 4-F—C$_6$H$_4$ | 2-Cl—C$_6$H$_4$ | Cl | N | 153-156° C. |

TABLE-continued $$\underset{\underset{OH}{|}}{\overset{\overset{X}{\underset{N}{\|}}\underset{N}{\searrow}}{\underset{A}{\overset{D}{\diagup}}\underset{}{\overset{}{\diagdown}}\underset{B}{\overset{}{\diagdown}}}}$$

| Ex | A | R | D | X | m.p./IR (cm$^{-1}$) |
|---|---|---|---|---|---|
| 2 | 4-F—C$_6$H$_4$ | 2-Cl—C$_6$H$_4$ | Br | N | 1503, 1413, 1213, 1126, 853, 752 |
| 3 | 4-F—C$_6$H$_4$ | 2-Cl—C$_6$H$_4$ | Cl | CH | 1509, 1228, 1069, 1057, 756 |
| 4 | 4-F—C$_6$H$_4$ | 2-Cl—C$_6$H$_4$ | Br | CH | |
| 5 | 4-F—C$_6$H$_4$ | 4-Cl—C$_6$H$_4$ | Cl | N | |
| 6 | 4-F—C$_6$H$_4$ | 4-Cl—C$_6$H$_4$ | Cl | CH | |
| 7 | 4-F—C$_6$H$_4$ | 2,4-Cl$_2$—C$_6$H$_3$ | Cl | N | |
| 8 | 4-F—C$_6$H$_4$ | 2,4-Cl$_2$—C$_6$H$_3$ | Cl | CH | |
| 9 | 4-F—C$_6$H$_4$ | 2,4-Cl$_2$—C$_6$H$_3$ | Br | N | |
| 10 | 4-F—C$_6$H$_4$ | C$_6$H$_5$ | Cl | N | |
| 11 | 4-F—C$_6$H$_4$ | C$_6$H$_5$ | Br | N | |
| 12 | 4-F—C$_6$H$_4$ | 2-Cl-4-F—C$_6$H$_3$ | Cl | N | |
| 13 | 4-F—C$_6$H$_4$ | 2-F—C$_6$H$_4$ | Cl | N | |
| 14 | 4-F—C$_6$H$_4$ | 2-F—C$_6$H$_4$ | Br | N | |
| 15 | 4-F—C$_6$H$_4$ | 2-F—C$_6$H$_4$ | Cl | CH | |
| 16 | 4-F—C$_6$H$_4$ | 4-F—C$_6$H$_4$ | Cl | N | |
| 17 | 4-F—C$_6$H$_4$ | 4-F—C$_6$H$_4$ | Br | N | |
| 18 | 4-F—C$_6$H$_4$ | 2,4-F$_2$—C$_6$H$_3$ | Cl | N | |
| 19 | 4-F—C$_6$H$_4$ | 2,4-F$_2$—C$_6$H$_3$ | Cl | CH | 1617, 1603, 1507, 1502, 1229, 1096, 964, 852 |
| 20 | 4-F—C$_6$H$_4$ | 2,4-F$_2$—C$_6$H$_3$ | Br | N | |
| 21 | 4-F—C$_6$H$_4$ | 2-Br—C$_6$H$_4$ | Cl | N | 160–169° C. |
| 22 | 4-F—C$_6$H$_4$ | 2-Br—C$_6$H$_4$ | Cl | CH | |
| 23 | 4-F—C$_6$H$_4$ | 2-Br—C$_6$H$_4$ | Br | N | |
| 24 | 4-F—C$_6$H$_4$ | 2-CF$_3$—C$_6$H$_4$ | Cl | N | 1508, 1163, 1123, 771 |
| 25 | 4-F—C$_6$H$_4$ | 2-CF$_3$—C$_6$H$_4$ | Cl | CH | |
| 26 | 4-F—C$_6$H$_4$ | 2-CF$_3$—C$_6$H$_4$ | Br | N | |
| 27 | 4-F—C$_6$H$_4$ | 2-CF$_3$—C$_6$H$_4$ | Br | CH | |
| 28 | 4-F—C$_6$H$_4$ | 4-CF$_3$—C$_6$H$_4$ | Cl | N | |
| 29 | 4-F—C$_6$H$_4$ | 4-CF$_3$—C$_6$H$_4$ | Cl | CH | 1510, 1326, 1126, 1067, 838 |
| 30 | 4-F—C$_6$H$_4$ | 4-NO$_2$—C$_6$H$_4$ | Cl | N | |
| 31 | 4-F—C$_6$H$_4$ | 4-NH$_2$—C$_6$H$_4$ | Cl | N | |
| 32 | 4-F—C$_6$H$_4$ | 2-CH$_3$—C$_6$H$_4$ | Cl | N | |
| 33 | 4-F—C$_6$H$_4$ | 2-CH$_3$—C$_6$H$_4$ | Cl | N | |
| 34 | 4-F—C$_6$H$_4$ | 4-CH$_5$O—C$_6$H$_4$ | Cl | N | |
| 35 | 4-F—C$_6$H$_4$ | 2-OCH$_3$—C$_6$H$_4$ | Cl | N | 1603, 1504, 1241, 1048, 756 |
| 36 | 4-F—C$_6$H$_4$ | 2-OCH$_3$—C$_6$H$_4$ | Cl | CH | |
| 37 | 4-F—C$_6$H$_4$ | 2-OCH$_3$—C$_6$H$_4$ | Br | N | |
| 38 | 4-F—C$_6$H$_4$ | 1-naphthyl | Cl | N | |
| 39 | 4-F—C$_6$H$_4$ | 2-naphthyl | Cl | N | |
| 40 | 4-F—C$_6$H$_4$ | 2-naphthyl | Cl | CH | |
| 41 | 4-F—C$_6$H$_4$ | tetrahydropyran-4-yl | Cl | N | |
| 42 | 4-F—C$_6$H$_4$ | cyclopropyl | Cl | N | |
| 43 | 4-F—C$_6$H$_4$ | cyclopentyl | Cl | N | |
| 44 | 4-F—C$_6$H$_4$ | cyclohexyl | Cl | N | |
| 45 | 4-F—C$_6$H$_4$ | 3-cyclohexenyl | Cl | N | |
| 46 | C$_6$H$_5$ | C$_6$H$_5$ | Cl | N | |
| 47 | C$_6$H$_5$ | 2-Cl—C$_6$H$_4$ | Cl | N | |
| 48 | C$_6$H$_5$ | 2-Cl—C$_6$H$_4$ | Cl | CH | |
| 49 | C$_6$H$_5$ | 2-Cl—C$_6$H$_4$ | Br | N | |
| 50 | C$_6$H$_5$ | 4-Cl—C$_6$H$_4$ | Cl | N | resin |
| 51 | C$_6$H$_5$ | 4-Cl—C$_6$H$_4$ | Cl | CH | resin |
| 52 | C$_6$H$_5$ | 2,4-Cl$_2$—C$_6$H$_3$ | Cl | N | 1506, 1276, 1133, 1100, 806, 701 cm$^{-1}$ |
| 53 | C$_6$H$_5$ | 2,4-Cl$_2$—C$_6$H$_3$ | Cl | CH | |
| 54 | C$_6$H$_5$ | 2-F—C$_6$H$_4$ | Cl | N | |
| 55 | C$_6$H$_5$ | 4-F—C$_6$H$_4$ | Cl | N | |
| 56 | C$_6$H$_5$ | 2-CF$_3$—C$_6$H$_4$ | Cl | N | |
| 57 | C$_6$H$_5$ | 2-CF$_3$—C$_6$H$_4$ | Cl | CH | |
| 58 | C$_6$H$_5$ | 4-CF$_3$—C$_6$H$_4$ | Cl | N | |
| 59 | C$_6$H$_5$ | 4-CF$_3$—C$_6$H$_4$ | Cl | CH | |
| 60 | C$_6$H$_5$ | 2-Br—C$_6$H$_4$ | Cl | N | |
| 61 | C$_6$H$_5$ | 2-Br—C$_6$H$_4$ | Cl | CH | |
| 62 | 4-Cl—C$_6$H$_4$ | C$_6$H$_5$ | Cl | N | |
| 63 | 4-Cl—C$_6$H$_4$ | 2-Cl—C$_6$H$_4$ | Cl | N | |
| 64 | 4-Cl—C$_6$H$_4$ | 2-Cl—C$_6$H$_4$ | Cl | CH | |
| 65 | 4-Cl—C$_6$H$_4$ | 4-Cl—C$_6$H$_4$ | Cl | N | |

TABLE-continued $$\begin{array}{c} X = \\ | \\ D\diagdown N \diagdown N \\ A \diagdown \diagup B \\ OH \end{array}$$

| Ex | A | R | D | X | m.p./IR (cm$^{-1}$) |
|---|---|---|---|---|---|
| 66 | 4-Cl—C$_6$H$_4$ | 4-Cl—C$_6$H$_4$ | Cl | CH | |
| 67 | 4-Cl—C$_6$H$_4$ | 2,4-Cl$_2$—C$_6$H$_3$ | Cl | N | |
| 68 | 4-Cl—C$_6$H$_4$ | 2,4-Cl$_2$—C$_6$H$_3$ | Cl | CH | |
| 69 | 4-Cl—C$_6$H$_4$ | 2-F—C$_6$H$_4$ | Cl | N | |
| 70 | 4-Cl—C$_6$H$_4$ | 2-F—C$_6$H$_4$ | Cl | CH | |
| 71 | 4-Cl—C$_6$H$_4$ | 4-F—C$_6$H$_4$ | Cl | N | |
| 72 | 4-Cl—C$_6$H$_4$ | 4-F—C$_6$H$_4$ | Cl | CH | |
| 73 | 4-Cl—C$_6$H$_4$ | 2-CF$_3$—C$_6$H$_4$ | Cl | N | |
| 74 | 4-Cl—C$_6$H$_4$ | 2-CF$_3$—C$_6$H$_4$ | Cl | CH | |
| 75 | 4-Cl—C$_6$H$_4$ | 4-CF$_3$—C$_6$H$_4$ | Cl | N | |
| 76 | 2-Cl—C$_6$H$_4$ | C$_6$H$_5$ | Cl | N | |
| 77 | 2-Cl—C$_6$H$_4$ | 2-Cl—C$_6$H$_4$ | Cl | N | |
| 78 | 2-Cl—C$_6$H$_4$ | 4-Cl—C$_6$H$_4$ | Cl | N | |
| 79 | 2-Cl—C$_6$H$_4$ | 2,4-Cl$_2$—C$_6$H$_3$ | Cl | N | |
| 80 | 2-Cl—C$_6$H$_4$ | 2-F—C$_6$H$_4$ | Cl | N | |
| 81 | 2-Cl—C$_6$H$_4$ | 4-F—C$_6$H$_4$ | Cl | N | |
| 82 | 2-Cl—C$_6$H$_4$ | 2-CF$_3$—C$_6$H$_4$ | Cl | N | |
| 83 | 2-F—C$_6$H$_4$ | C$_6$H$_5$ | Cl | N | |
| 84 | 2-F—C$_6$H$_4$ | 2-Cl—C$_6$H$_4$ | Cl | N | |
| 85 | 2-F—C$_6$H$_4$ | 4-Cl—C$_6$H$_4$ | Cl | N | |
| 86 | 2,4-Cl$_2$—C$_6$H$_3$ | 2-Cl—C$_6$H$_4$ | Cl | N | |
| 87 | 2,4-Cl$_2$—C$_6$H$_3$ | 4-Cl—C$_6$H$_4$ | Cl | N | |
| 88 | 2,4-Cl$_2$—C$_6$H$_3$ | 4-F—C$_6$H$_4$ | Cl | N | |
| 89 | p-biphenyl | C$_6$H$_5$ | Cl | N | |
| 90 | cyclohexyl | C$_6$H$_5$ | Cl | N | |
| 91 | cyclohexyl | 2-Cl—C$_6$H$_4$ | Cl | N | |
| 92 | cyclohexyl | 4-Cl—C$_6$H$_4$ | Cl | N | |
| 93 | cyclohexyl | 2,4-Cl$_2$—C$_6$H$_3$ | Cl | N | |
| 94 | cyclohexyl | 2,4-Cl$_2$—C$_6$H$_3$ | Cl | CH | |
| 95 | cyclohexyl | 2-Br—C$_6$H$_4$ | Cl | N | |
| 96 | cyclohexyl | 2-Br—C$_6$H$_4$ | Cl | CH | |
| 97 | cyclohexyl | 2-F—C$_6$H$_4$ | Cl | N | |
| 98 | cyclohexyl | 4-F—C$_6$H$_4$ | Cl | N | |
| 99 | cyclohexyl | 4-F—C$_6$H$_4$ | Br | N | |
| 100 | cyclohexyl | 2-CF$_3$—C$_6$H$_4$ | Cl | N | |
| 101 | cyclohexyl | 4-CF$_3$—C$_6$H$_4$ | Cl | N | |
| 102 | cyclohexyl | 3-pyridyl | Cl | N | |
| 103 | tert.-C$_4$H$_9$ | C$_6$H$_5$ | Cl | N | |
| 104 | tert.-C$_4$H$_9$ | 2-Cl—C$_6$H$_4$ | Cl | N | |
| 105 | tert.-C$_4$H$_9$ | 4-Cl—C$_6$H$_4$ | Cl | N | |
| 106 | tert.-C$_4$H$_9$ | 2,4-Cl$_2$—C$_6$H$_3$ | Cl | N | |
| 107 | tert.-C$_4$H$_9$ | 2-Br—C$_6$H$_4$ | Cl | N | |
| 108 | tert.-C$_4$H$_9$ | 2-F—C$_6$H$_4$ | Cl | N | |
| 109 | tert.-C$_4$H$_9$ | 4-F—C$_6$H$_4$ | Cl | N | |
| 110 | tert.-C$_4$H$_9$ | 2-CF$_3$—C$_6$H$_4$ | Cl | N | |
| 111 | tert.-C$_4$H$_9$ | 4-CF$_3$—C$_6$H$_4$ | Cl | N | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The application rates of the fungicidal agents depends on the type of effect desired and varies from 0.02 to 3 kg of active ingredient and more. The novel active ingredients may also be used for protecting materials, e.g., against Paecilomyces variotii.

The novel compounds may exercise a variety of influences on practically all plant development stages, and are therefore used as growth regulators. The diversity of action of growth regulators depends especially on
a) the type and variety of plant;
b) the time applied, with reference to the development stage of the plants and the time of the year;
c) the place and method of application (seed treatment, soil treatment, or application to foliage);
d) climatic factors, e.g.: average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

Of practical importance is the reduction in vegetative growth in fruit trees and other woody plants, thus saving pruning costs.

The use of growth regulators is also important for inhibiting plant height and changing the time of ripening in cotton. It is thus possible for this important crop to be harvested completely mechanically.

Growth regulators may also increase or inhibit lateral branching. This is of interest when for instance in tobacco plants it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g per kg of seed are generally required. For foliage and soil treatment, amounts of from 0.01 to 10, and preferably from 0.02 to 3, kg/ha are generally considered to be sufficient.

The novel substances may be converted into conventional formulations such as solutions emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), amines (e.g., ethanolamine, dimethylformamide), and water; carriers such as ground natural minerals (e.g., kaolins aluminas talc and chalk) and ground synthetic minerals (e.g., highly disperse silica and silicates); emulsifiers and other surfactants, such as nonionic and anionic emulsifiers (e.g., polyoxyethylene fatty alcohol ethers, alkyl sulfonates); and dispersants such as lignin, sulfite waste liquors and methylcellulose.

The fungicidal agents generally contain from 0.1 to 95 and preferably from 0.5 to 90, wt % of active ingredient.

The agents and the ready-to-use formulations prepared from them, such as solutions, emulsions suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 24 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 19 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 29 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 24 is intimately mixed with 10 parts by weight of the sodium salt of a phenolsulfonic acid-ureaformaldehyde condensate, 2 parts of silica gel and 48 parts of water to give a stable aqueous dispersion. Dilution in water gives an aqueous dispersion.

IX. 20 parts by weight of compound no. 19 is intimately mixed with 2 parts by weight of the calcium salt of dodecylbenzenesulfonic acid 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

Use examples

For comparison purposes, the compounds 1-(1,2,4-triazol-1-yl)-2-(4-chlorophenyl)-3-phenylprop-1-en-3-ol (A) and 1-(1,2,4-triazol-1-yl)-2-(4-chlorophenyl)-3-(2,4-dichlorophenyl)-prop-1-en-3-ol (B) disclosed in EP 23,286 were used.

USE EXAMPLE 1

Action on *Pyricularia oryzae* (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of Pyricularia oryzae. The plants were then set up in climatic cabinets at from 22° to 24° C. and a relative humidity of 95 to 99%. The extent of fungus spread was assessed after 6 days.

The results show that active ingredients 1, 2, 19 and 29, applied as 0.05 wt % spray liquors, had a better fungicidal action (90%) than prior art comparative agent B (4%).

USE EXAMPLE 2

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 1, 2, 3 and 24, applied as 0.006wt % spray liquors, have a better fungicidal action (95%) than prior art comparative agent B (40%).

USE EXAMPLE 3

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus Pyrenophora teres, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 2, 3, 19, 29 and 51, applied as 0.05 wt % spray liquors have a better fungicidal action (90) than prior art active ingredients A and B (0%).

To determine the growth-regulating properties of the candidate compounds, the test plants were grown in plastic pots (approx. 12.5 cm in diameter, and having a volume of about 500ml) in a substrate provided with sufficient nutrients.

In the preemergence treatment method the candidate compounds were sprayed as aqueous formulations onto the seedbed on the day of sowing. In the postemergence method, the compounds were sprayed as aqueous formulations onto the plants.

The growth-regulating action observed was confirmed at the end of the experiment by measuring the height of the plants. The figures obtained were compared with the growth height of the untreated plants.

USE EXAMPLE 4

TABLE 1

| | Spring wheat "Ralle" variety Postemergence (leaf) treatment | |
|---|---|---|
| Active ingr. | Conc. mg of a.i./vessel | Growth height relative in % |
| untreated | — | 100 |
| A | 6 | 100 |
| 1 | 6 | 92.8 |
| 19 | 6 | 94.4 |
| B | 6 | 100 |
| 50 | 6 | 88.9 |

TABLE 2

| | Spring barley, "Aramir" variety Preemergence (soil) treatment | |
|---|---|---|
| Active ingr. | Conc. mg of a.i./vessel | Growth height relative in % |
| untreated | — | 100 |
| A | 6 | 100 |
| 1 | 6 | 93.9 |

TABLE 3

| | Spring barley, "Aramir" variety Postemergence (leaf) treatment | |
|---|---|---|
| Active ingr. | Conc. mg of a.i./vessel | Growth height relative in % |
| untreated | — | 100 |
| A | 6 | 100 |
| 19 | 6 | 90.2 |

TABLE 4

| | Sunflowers, "Spanners Allzweck" variety Postemergence (leaf) treatment | |
|---|---|---|
| Active ingr. | Conc. mg of a.i./vessel | Growth height relative in % |
| untreated | — | 100 |
| B | 6 | 100 |
| 29 | 6 | 86.4 |

We claim:

1. A compound of the formula

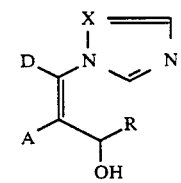

wherein A and R are each independently selected from the group consisting of $C_5$-$C_8$-cycloalkenyl; tetrahydropyranyl; naphthyl; naphthyl substituted by halogen, nitro, phenoxy, amino, alkyl of 1 to 4 carbon atoms, alkoxy of 1 to 4 carbon atoms or haloalkyl of 1 to 4 carbon atoms; phenyl; and phenyl substituted with nitro, phenoxy, amino, alkoxy of 1 to 4 carbon atoms, haloalkyl of 1 to 4 carbon atoms, or halo; D is selected from the group consisting of chloro and bromo; and X is N; or acid addition salts or metal complexes thereof which are tolerated by plants.

2. A compound of claim 1, wherein A and R are both phenyl which is unsubstituted or bears 1 or 2 substituents selected from the group consisting of fluorine, chlorine, bromine and trifluoromethyl.

3. A compound of claim 1, wherein A is 4-fluorophenyl, R is 2-chlorophenyl, and D is chloro.

4. A compound of claim 1, wherein A is 4-fluorophenyl, R is 2-chlorophenyl, and D is bromo.

5. A compound of claim 1, wherein A is 4-fluorophenyl, R is 2-trifluoromethylphenyl, and D is chloro.

6. A fungicidal composition comprising a carrier and a fungicidally effective amount of a compound according to claim 1.

7. A process for combating fungi, wherein a fungicidally effective amount of a compound of claim 1 is applied to the fungi or to the plant materials, plant spaces, plants or seeds threatened by fungus attack.

* * * * *